United States Patent [19]

Gordon et al.

[11] Patent Number: 4,834,019
[45] Date of Patent: May 30, 1989

[54] TISSUE SPECIMEN TREATMENT APPARATUS

[75] Inventors: Alan J. Gordon, Liverpool; David J. Bowman, Denton; Jeffrey E. Lockett; Michael Murry, both of Runcorn, all of United Kingdom

[73] Assignee: Shandon Scientific Limited, Cheshire, England

[21] Appl. No.: 125,348

[22] Filed: Nov. 25, 1987

[30] Foreign Application Priority Data

Nov. 27, 1986 [GB] United Kingdom ............... 8628371

[51] Int. Cl.⁴ .................................... B05C 3/02
[52] U.S. Cl. ........................ 118/423; 118/426; 118/50
[58] Field of Search ................ 118/423, 426, 50

[56] References Cited

U.S. PATENT DOCUMENTS

| | | | |
|---|---|---|---|
| 2,324,122 | 7/1943 | Welskopf | 118/425 X |
| 2,788,068 | 4/1957 | Blumenfeld | 161/1 |
| 2,872,893 | 2/1959 | Kling | 118/426 X |
| 3,110,627 | 11/1963 | Welskopf | 118/426 X |
| 3,762,362 | 10/1973 | Lipshaw | 118/5 |
| 3,809,008 | 5/1974 | Takahashi | 118/6 |
| 4,099,483 | 7/1978 | Henderson | 118/49.1 |

FOREIGN PATENT DOCUMENTS

2163568A  2/1986  United Kingdom .

*Primary Examiner*—Shrive P. Beck
*Assistant Examiner*—Alain Bashore
*Attorney, Agent, or Firm*—Vaden, Eickenroht, Thompson & Boulware

[57] ABSTRACT

Tissue specimen treatment apparatus of the multi-chamber type having a plurality of containers, for instance arranged in a circle, and means for transporting a specimen for treatment to selected such chambers in a prescribed sequence, is characterized by a containment vessel disposed about at least the open tops of the containers and by cover means movable with the transporting means and evelosing the interior of the containment vessel so as to separate the specimen from the ambient atmosphere. The cover means preferably closely overlies the open tops of the containers to minimize the volume of the containment vessel, and is formed with a small volume transfer enclosure to receive a specimen during transport. The cover may have a close fit to the containment vessel, sufficient to restrict exchange of gases etc. between the external atmosphere and the containment vessel, or more positive sealing arrangements may be provided—e.g. labyrinth, flexible or liquid seals—to prevent flows between the vessel and the environment. Additionally or alternatively, positive venting of the containment vessel by withdrawal of its atmosphere may ensure that all leakages are into the vessel.

13 Claims, 6 Drawing Sheets

TISSUE SPECIMEN TREATMENT APPARATUS

FIELD OF THE INVENTION

The invention relates to apparatus for treatment of histological and like tissue specimens by sequential treatment with a series of reagents.

BACKGROUND TO THE INVENTION AND THE PRIOR ART

Typically in the preparation of tissue specimens for microscopic examination, the specimens are subjected progressively to fixation, dehydration, clearing and embedding in a suitable wax to facilitate sectioning of the tissue specimens. The sectioned specimens may then be further treated to permit their staining and mounting for examination. The dehydration stage usually involves the treatment of a batch of specimens with alcohol reagents of progressively increasing concentration, and the clearing stage involves the treatment of these dehydrated specimens one or more times with a clearing agent such as xylene to displace the alcohol. An analogous preparation technique now coming into favour substitutes a resin impregnation/embedding stage for the wax-embedding procedure that conventionally follows the described dehydration and clearing stages. The resin impregnation/embedding stage may, for instance, consist in first impregnating the dehydrated specimens with a resin solution containing an inhibited activator, followed by infiltrating the impregnated specimens with a hardener solution that enables the activator to accomplish curing of the resin. The treatment of sectioned specimens for staining typically involves dewaxing or etching and rehydration in one or more stages, and the staining procedure (using aqueous stains or immunostaining techniques) is usually followed by a treatment with an agent compatible with the mountant used for coverslipping the section.

Apparatus used for these treatments falls into two general classes: single-container appratus as discussed below; and multi-container apparatus in which there is a plurality of containers that in use respectively contain the various individual reagents, a specimen or a batch of specimens, typically contained, perhaps in cassettes, in an openwork basket, being transported to each (or a selection) of the containers in a prescribed sequence to be immersed in the respective reagents therein to accomplish the required treatment steps. Typically the reagent-containing containers are disposed in a circle and a specimen basket is supported on a radial arm so as to be capable of being raised and lowered into and out of a selected container, relative rotation between the arm and the circle of containers serving to position the basket for introduction into a particular container. Modern apparatus of this type is significantly automated and capable of carrying out a treatment sequence involving immersion of tissue specimens, in the basket, for selected individual periods of time in a preselected sequence of the reagent-containing containers.

In general, apparatus of this multi-container type is so arranged that there is considerable exposure of the tissue specimens to the ambient atmosphere in the intervals between successive immersions of the specimens in the respective reagents. Because the reagents are, typically, volatile there is substantial loss of reagent vapour to the local atmosphere as well as the risk of reagent splashing and contamination of the environment of the apparatus. Moreover, sometimes the tissue specimens to be treated are noxious or toxic so that their unrestrained exposure to ambient atmosphere gives rise to unacceptable local contamination, necessitating operation of the apparatus within an appropriate enclosure.

Both to mitigate this problem of environmental contamination and to provide other advantages, there has recently been developed the single-container apparatus in which there is a single processing container for the reception of one or more tissue specimens and to which reagents are supplied, in turn, for the sequential treatment of the tissue specimen(s) therein with such reagents. An example of an apparatus of this kind is disclosed, for instance, in U.S. Pat. No. 4,604,964 (Gordon et al) that provides for substantially total containment within the apparatus, during the operation thereof, of the specimen(s) being treated, all the reagent liquids and any vapours thereof. Such single-container apparatus is, however, typically of considerably greater capital cost than multi-chamber apparatus and an objective of the present invention is to provide a multi-container apparatus that is so constructed and arranged as to achieve substantial containment of specimens, reagent liquids and their vapours within the confines of the apparatus during operation thereof, thereby to obtain the containment advantages of the single-container apparatus without the concomitant cost and complexity.

SUMMARY OF THE INVENTION

The invention consists in tissue specimen treatment apparatus, of the multi-chamber type comprising a plurality of containers and means for transporting a specimen for treatment to selected said containers in a prescribed sequence, that is characterised by a containment vessel disposed about at least the open tops of said containers, and cover means movable with said transporting means and enclosing the interior of said vessel so as to separate the specimen from the ambient atmosphere.

In this apparatus, the containment vessel and the cover means jointly serve to separate a specimen for treatment is also contained during its transport from container to chamber and while positioned in a said container, whereby uncontrolled escape of treatment reagents and material from the specimen, to the external ambient atmosphere, is at least substantially avoided.

Desirably the cover means is positioned to be adjacent to and to overlie open tops of the said containers and includes, a transfer enclosure adapted to register with the open top of a selected container to receive a specimen during transport thereof. As a consequence of this configuration the enclosed volume of the containment vessel is minimised thereby to minimise the evaporation of reagents in the said containers and also to minimise the volume of gas and vapour displaced from within the containment vessel during substitution of one specimen by another.

Preferably the transfer enclosure of the cover means has an access hatch therein to provide for the introduction and removal of specimens without the necessity to remove the cover means. This feature also minimises escape of gases and vapours within the containment vessel to the ambient atmosphere during exchange of specimens.

Conveniently the said cover means encloses an operating head comprising the said transporting means.

In preferred embodiments of the invention the said containers are arranged in a circle and the containment vessel is circular in plan, so that transport of a specimen between containers involves simple indexing movement of the cover means about an axis coincident with the centre of the circle of said containers. Other arrangements are however possible.

Desirably the apparatus comprises a central engine unit housing, e.g., an electric motor for driving the transporting means and for indexing the cover means relatively to the containers. The engine unit may conveniently provide a support for a horizontal deck that in turn provides support for the containers and constitutes the lower wall of the containment vessel. A peripheral flange on this deck may then constitute the peripheral wall of the containment vessel.

The apparatus may include chamber heating means for heating at least one of the chambers: for instance for heating a container intended to contain wax. The container heating means may suitably comprise an electrical heating element associated with the or each container to be heated.

Various further features of preferred embodiments of the invention will appear from the following description with reference to the accompanying drawings.

DESCRIPTION OF PREFERRED EMBODIMENTS OF THE INVENTION

Figure 1:
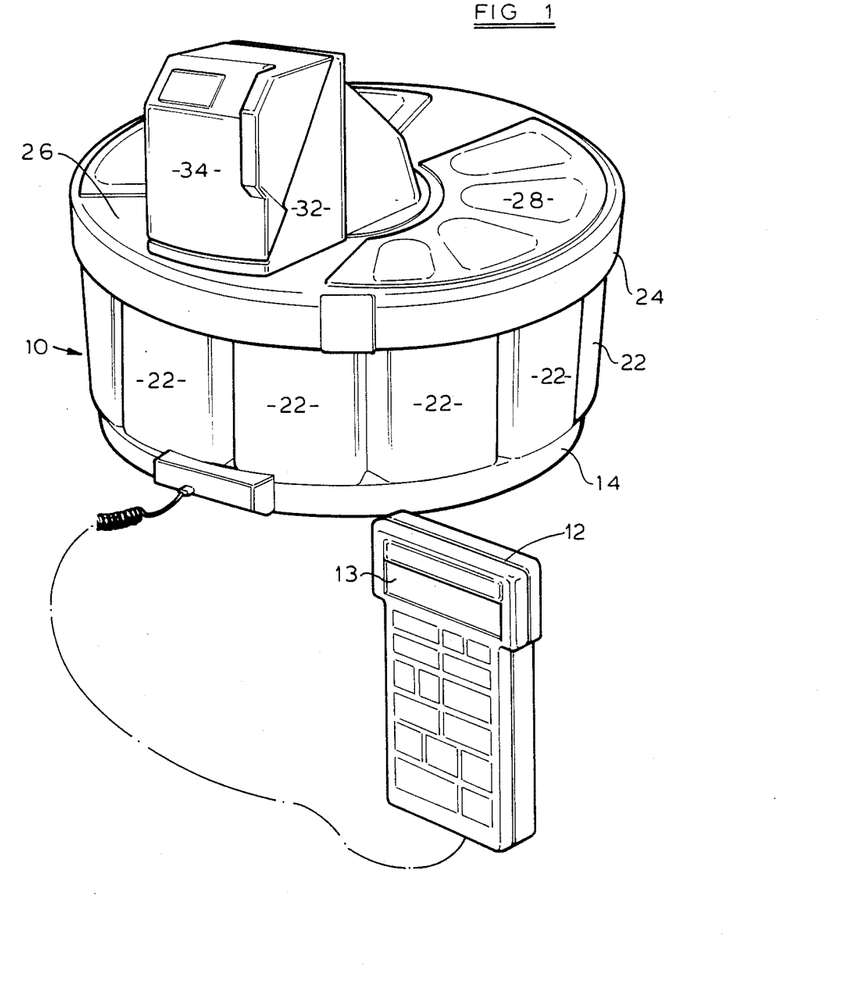
FIG. 1 is a perspective view of a tissue specimen treatment apparatus embodying the invention.

Referring to the drawings, FIG. 1 shows that the apparatus of this embodiment comprises a generally drum-like processing module 10 having an umbilical connection to a hand-held command module 12. The command module 12 provides function and programming controls and displays on a front panel 13. While the processing module 10 and the command module 12 are shown in FIG. 1 as being separated and connected by an umbilical, in other embodiments of the invention these modules are united.

The processing module 10 comprises a circular platform 14 that supports (FIG. 2) a central engine unit 16 housing an electric motor 18. The engine unit 16 carries a horizontal deck 20 having openings 21 to receive the open tops of a set of reagent containers 22 that in use are disposed in a circle about the central axis of the engine unit 16. The chambers 22 have a truncated sector-shaped plan section and fit the openings 21, the chambers having flanges 23 that rest on the deck 20 to provide a closure of the openings. Seals may be provided under the flanges 23 to obtain sealing to the deck 20, if required.

Figure 2:
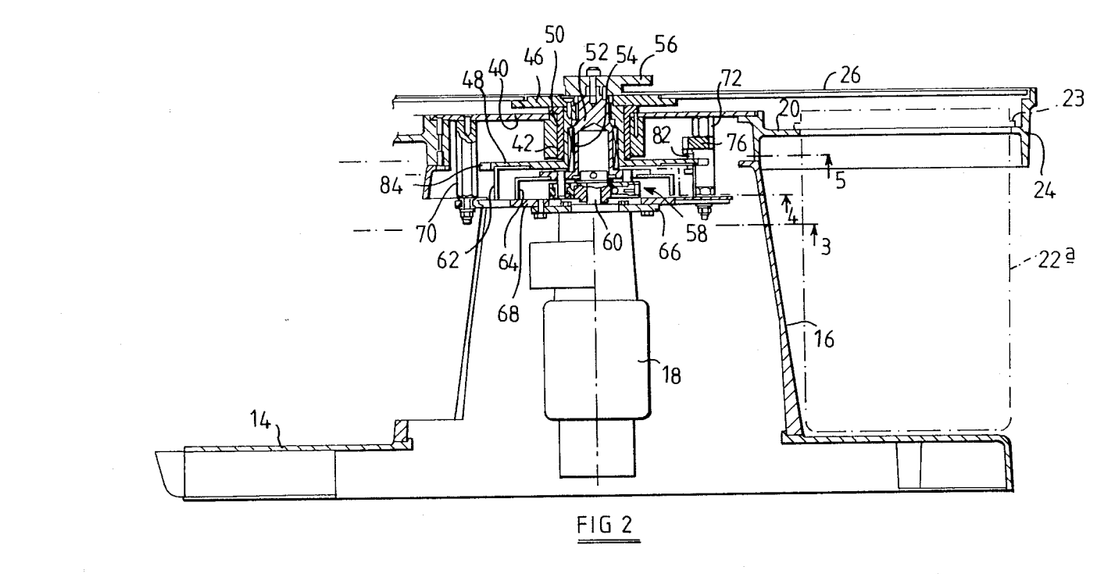
FIG. 2 is a vertical fragmentary sectional view of the apparatus of FIG. 1, taken on line 2—2 of FIG. 3.
Figure 3:
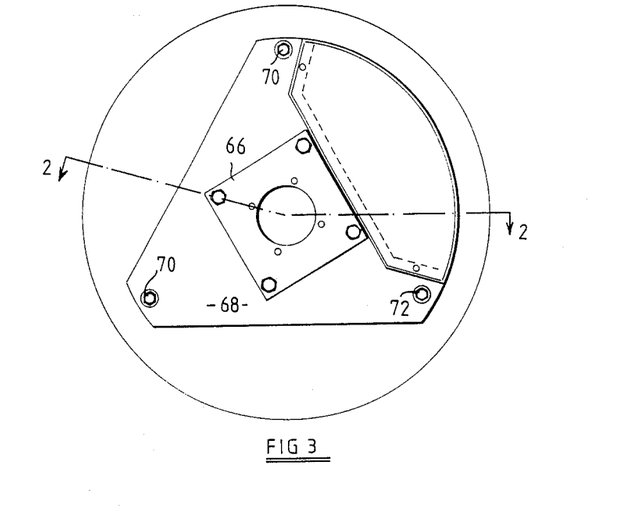
FIG. 3 is a sectional view on the line 3—3 of FIG. 2.

The deck 20 has a vertical peripheral flange 24 that forms the peripheral wall of a containment vessel the bottom wall of which is constituted by the deck 20.

In this embodiment there are twelve containers 22, ten for containing treatment reagents and two for containing wax. The outline of a reagent container 22a is shown at the righthand side of FIG. 2, and the configuration of the upper part of a typical container 22 is shown in section in FIG. 8.

All the chambers 22 are supported so that their tops are at a common level, just below the top of the flange 24 of the deck 20.

A circular disc-like cover 26 overlies the tops of the containers 22 and is dimensioned to fit within the flange 24 with a small clearance (e.g. 0.5 mm) so as to provide a top wall of the containment vessel. The cover 26 is arranged for rotation about its centre and has three openings, two openings 27 providing access to containers 22 therebelow for servicing purposes, such as refilling with reagent or exchange, and being normally closed by removable lids 28, while the third, smaller, opening 30 matches the plan section of the containers and serves as a port for the introduction of specimens into a container over which the opening 30 is positioned, by the operation of the transport mechanism to be described. The opening 30 communicates with a transfer enclosure 32 on the top of the cover 26 and that houses specimen manipulating mechanism. The transfer enclosure 32 has a removable front wall 34 providing a hatch through which specimens may be introduced into the enclosure for treatment, or be withdrawn from the enclosure after treatment.

The transport mechanism comprises means for indexing the cover 26 relatively to the deck 20 so as to bring the opening 30 and transfer enclosure 32 into position over selected chambers 22, in a predetermined sequence. For this purpose the central engine unit 16 includes a mounting plate 40 to which the deck 20 is fixed and that has a central aperture fitted with a sleeve bearing 42 for a head carrier assembly 44 comprising upper and lower plates 46, 48, respectively at the upper and lower ends of a hollow journal 50 rotatable in the bearing sleeve 42.

The journal 50 is constituted by a sleeve rotatable about a central driveshaft 52 to which it is coupled by a freewheel 54. At its upper end, the central driveshaft 52 carries a lift cam 56 while the lower end of the shaft 52 is connected by a torque-limiting coupling 58 to the driveshaft 60 of the motor 18.

The upper plate 46 of the head carrier assembly carries the cover 26 that has a central aperture to provide clearance for the lift cam 56, while the lower plate 48 of the head carrier assembly carries a skirt-like position encoder 62 that coacts with an optical reading device (not shown) to signal the rotational position of the head carrier assembly relatively to the engine unit 16.

The drive motor coupling 58 carries a similar skirt-like position encoder 64 that cooperates with an optical reading device for signalling the rotational position of the lift cam 56 relatively to the engine unit 16.

The housing of the motor 18 is secured by an end-plate 66 to a mounting plate 68 that is in turn suspended from the mounting plate 40 of the engine unit 16, by means of two pillars 70 and a pivot post 72.

Latching means are provided for latching the head carrier assembly in preselected indexed positions relatively to the engine unit 16. These latching means are illustrated in FIGS. 2, 4, 5 and 6 and comprise a crank lever pivoted between its ends on the pivot post 72 so as to project lever arms 74 and 76 disposed at an included angle of about 130°. The arm 74 is articulated by a link 78 to a solenoid 80 fixed to the underside of the mounting plate 40, whereas the extremity of the arm 76 carries a detent roller 82 adapted for engagement in peripheral notches 84 in the lower plate 48 of the head carrier assembly.

The crank lever comprising the arms 74, 76 is urged to rock in a clockwise direction, as seen from below in FIGS. 4 and 5, by means of a spring loaded thruster pin 86 articulated to a trunion 88 on the arm 74 and encircled by a spring 90 acting between the head of pin 86 and a support bracket 92 on the underside of the mounting plate 40.

Figure 4:
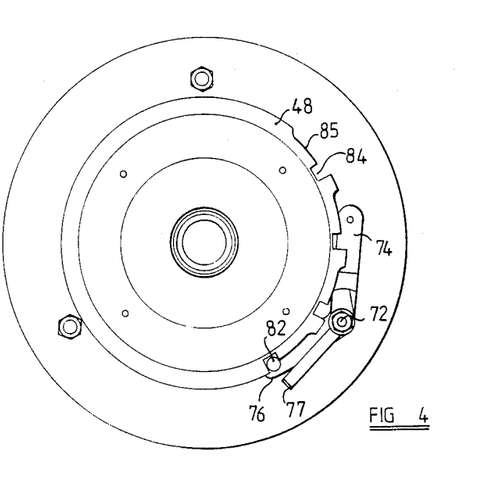
FIG. 4 is a sectional view on the line 4—4 of FIG. 2.
Figure 5:
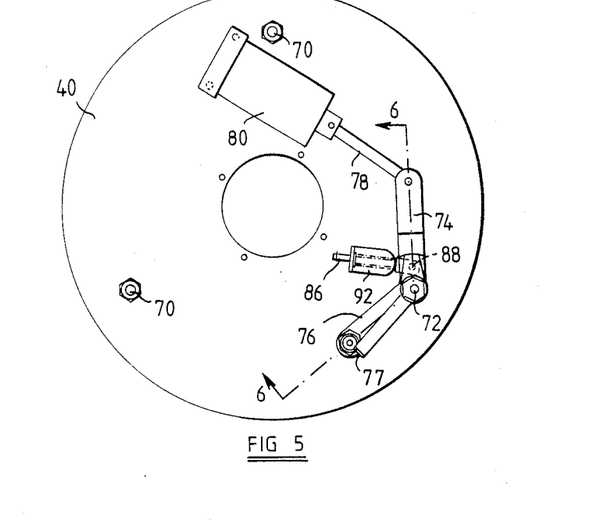
FIG. 5 is a sectional view on the line 5—5 of FIG. 2.
Figure 6:
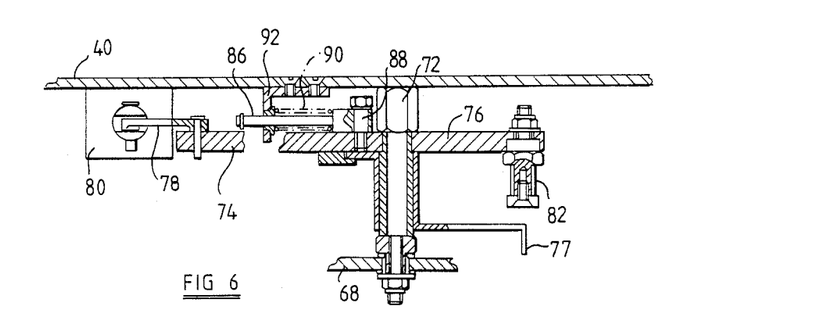
FIG. 6 is a sectional view on the line 6—6 of FIG. 5.

As best seen in FIG. 4, the notches 84 in the periphery of the lower plate 48 of the head carrier assembly are each associated with a run-in step 85 on which the detent roller 82 may run as the head carrier assembly is being indexed to approach a selected indexed position in which it will be retained by engagement of the detent roller 82 in the associated notch 84.

A signalling arm with a down-turned extremity 77 is associated with the crank lever to move therewith and to signal the position of the latter by means of an optical reading device (not shown).

Figure 7:
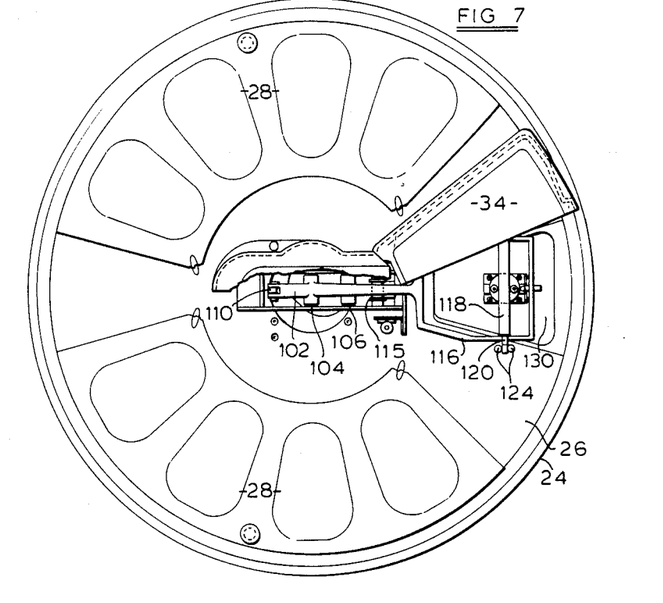
FIG. 7 is a part-sectional plan view.
Figure 8:
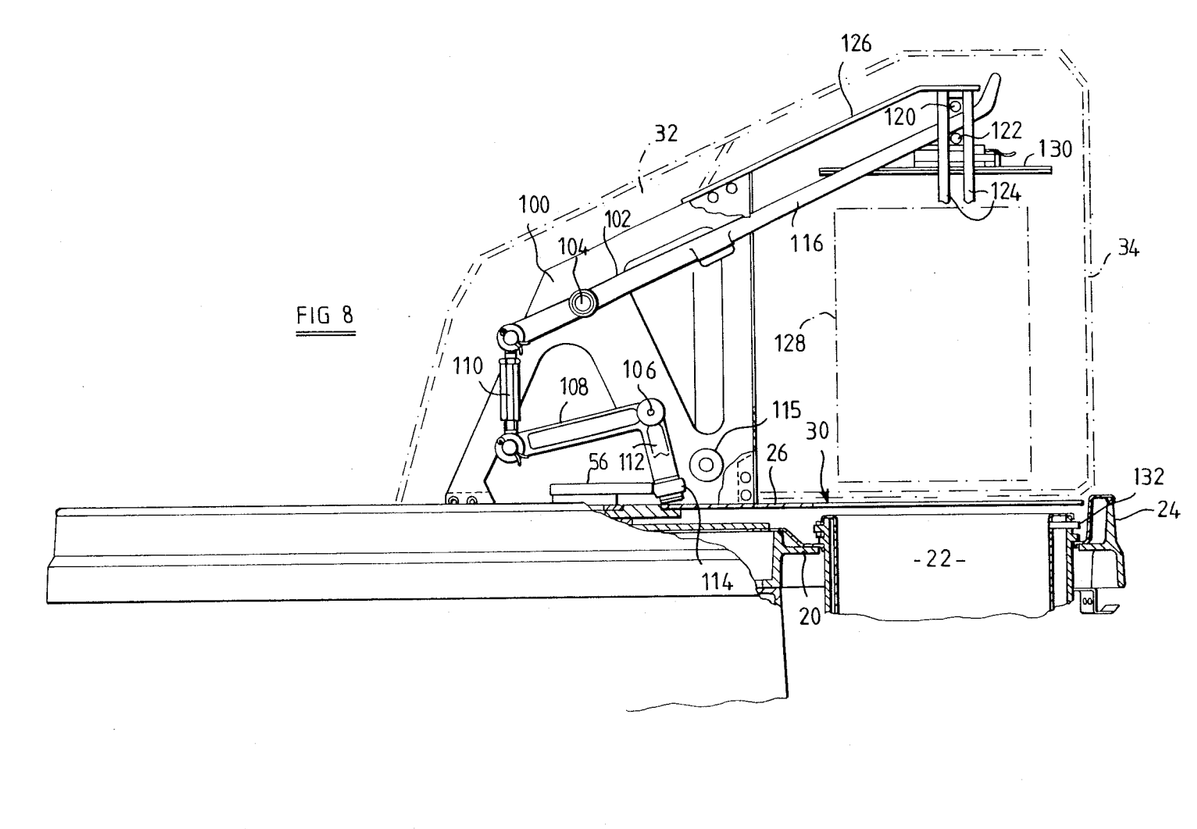
FIG. 8 is a part-sectional view of the transport mechanism.

As noted, the transfer enclosure 32 houses specimen manipulating mechanism the construction of which is best seen in FIGS. 7 and 8. This mechanism comprises a support frame 100 fixed to the upper plate 46 of the head carrier assembly so as to be indexible therewith relatively to the engine unit 16. The support frame 100 is constituted by a pair of parallel side plates between which a carrier arm 102 is rockable in a vertical plane on a pivot shaft 104 carried by the plates of the frame 100. Another pivot shaft 106 extending between the plates of the frame 100 pivotally supports an operating crank having one arm 108 articulated through an adjustable link 110 to the adjacent end of the carrier arm 102. A second arm 112 of the crank extends downwardly and carries a follower roller 114 that engages the periphery of the lift cam 56, the arrangement being such that rotation of the cam 56 relatively to the head carrier assembly rocks the crank and thus the carrier arm 102. The carrier arm is spring-loaded by a Tensator spring 115 to hold the follower roller 114 in engagement with the lift cam 56.

The other end of the carrier arm 102 is bifurcated to constitute a yoke 116 the limbs of which support a crossbar 118 (FIG. 7) by engaging between guide pins 120, 122 on the ends of the crossbar and that extend beyond the yoke limbs and coact with vertical guide rails 124, the latter being carried by the cover 26 on each side of the opening 30 therein, and by a plate 126 forming part of the support frame 100.

The crossbar 118 supports a specimen basket that is not shown in detail because it may take a variety of different configurations but the general location of which is indicated by the broken outline 128 in FIG. 8. It will be apparent that the crossbar 118 is constrained by the guide rails 124 to move vertically in response to rocking of the carrier arm 102 about its pivot shaft 104, the arcuate movement of the limbs of the yoke 116 being accommodated by movement thereof between the guide pins 120, 122 at each end of the crossbar 118.

As indicated in FIG. 8, the crossbar 118 may carry a lid 130 intended to pass through the opening 30 in the cover 26 when the crossbar 118 is lowered to lower the specimen basket 128 into a container 22 over which the opening 30 is positioned, and to engage the top of that container to minimise escape of gas and vapour therefrom. The lid 130 may be arranged to provide an effective seal for the top of the container 22 so as to enable the interior of the latter to be subjected to reduced atmospheric pressure during, the treatment of tissue specimen(s) therein. The container 22 illustrated in FIG. 8 is shown as having a vent 132 for connection to a vacuum pump or the like for such purposes.

Figure 9:
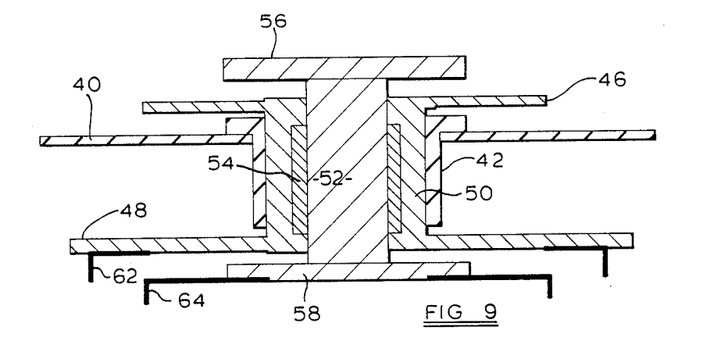
FIG. 9 is a diagrammatic section of the drive for the transport mechanism.

The operation of the apparatus and in particular the manner in which the motor 18 accomplishes both indexing of the head carrier assembly and rocking of the carrier arm 102 to raise and lower the specimen basket 128, is best understood with reference to the diagrammatic illustration of FIG. 9.

The lift cam 56 is so shaped that when rotated through one complete revolution relatively to the head carrier assembly it causes the carrier arm 102 to perform one complete rocking excursion about its pivot shaft 104.

The lift cam 56 is free to rotate relatively to the head carrier assembly in one direction only, because of the action of the freewheel 54. The arrangement is such that when the drive motor 18 rotates the coupling 58 and thus the drive shaft 52 and lift cam 56 in an anticlockwise direction as viewed from above, the free-wheel 54 does not transmit torque to the head carrier assembly and this may therefore remain latched in position relatively to the engine unit 16 by reason of engagement of the detent roller 82 in one of the peripheral notches 84 of the lower plate 48 of the head carrier assembly.

However, clockwise rotation of the assembly of coupling 58, driveshaft 52 and lift cam 56 by the motor 18 results in torque being transmitted by the freewheel 54 to the head carrier assembly to tend to turn this in a clockwise direction in unison with the lift cam. Such rotation of the head carrier assembly can be permitted by disengagement of the detent roller 82, by the actuation of the solenoid 80 to rock the crank lever arms 74, 76 in opposition to the thrust of the spring pressed pin 86.

In use of the illustrated apparatus, assuming that one or more specimens—loaded for instance into cassettes—have been placed in the specimen basket 128 with the latter in its raised position as illustrated in FIG. 8, the control module 12 is programmed to cause the specimen basket to be transported, by clockwise rotation of the head carrier assembly, until the opening 30 in the cover 26 is disposed above that container 22 which contains the first reagent into which the specimen(s) are to be immersed for treatment; thereafter to cause lowering of the specimen basket, to immerse the specimen(s) in the reagent in that container; to hold the basket 128 so immersed for a prescribed duration; then to lift the basket 128 out of the container 22, through the opening 30 into the transfer enclosure; and thereafter by further clockwise rotation of the head carrier assembly, to position the opening 30 over the container 22 containing the reagent in which the specimen(s) are next to be immersed; and so on.

The control arrangements of the command module provide for operation of the drive motor 18 selectively clockwise and anticlockwise as required to produce the desired movements of the head carrier assembly and of the specimen basket respectively, and for operation of the solenoid 80 to unlatch the head carrier assembly when indexing movement of the head carrier assembly is required. The controls of the command module react to signals from the optical reading devices (not shown) that identify the positions of the lift cam and head carrier assembly, respectively, relatively to the (stationary) engine unit 16, and to signals from the optical reading device that detects the position of the signalling arm extremity 77 to signal the position of the crank arms 74 and 76 and thereby to provide for interlocking of the operation of the drive motor with operation and release of the solenoid 80.

In this connection, when the command module initiates indexing of the head carrier assembly to position the cover opening 30 above a particular chamber 22, the interlocking arrangements verify that the position of the lift cam is such that the specimen basket 128 is in its fully raised position, whereafter the solenoid 80 is actuated to withdraw the detent roller 82 from the notch 84 in which it had been lodged. The drive motor 18 is then activated to drive the coupling 58 in a clockwise direction so that the lift cam and the head carrier assembly are caused by the freewheel 54 to rotate together as a unit, whereby there is no relative rotation between the lift cam and the head carrier assembly to cause vertical motion of the specimen basket. Clockwise indexing motion of the head carrier assembly thus takes place with the specimen basket held in the raised position.

When the head carrier assembly is approaching the position in which the cover opening 30 registers with the required container 22—a circumstance signalled to the command module by the optical reading device cooperating with the head position encoder 62—the solenoid 80 is released to permit the detent roller 82 to move inwardly towards the periphery of the plate 48 and to enter the run-in step 85 associated with the notch 84 that determines the exact desired indexed position of the head carrier assembly. The consequent movement of the signalling arm extremity 77 signals the command module to reduce the speed of the drive motor 18 as it approaches the position in which it is to come to rest. When the exact required position is reached, the detent roller 82 drops into the notch 84, positively to arrest the head carrier assembly and to retain it in the required indexed position. The further movement of the signalling arm extremity 77 signals the command module to stop the motor 18 and to prepare the motor next to drive the coupling 58 in an anticlockwise direction thereby to rotate the lift cam 56 relatively to the head carrier assembly and so cause lowering of the specimen basket 128 into the container 22 over which it has been positioned by the preceding indexing motion of the head carrier assembly.

Anticlockwise rotation of the drive motor 18 is maintained until the specimen basket 128 has been lowered fully into the container 22 (after having been dunked therein one or more times if the treatment routine so requires) whereupon the command module stops the drive motor in response to a signal from the optical reading means cooperating with the lift cam position encoder 64.

The illustrated apparatus may be modified in various ways to adapt it for particular uses. Thus, for instance, while for general purpose use a reasonably close fit between the cover 26 and the flange 24 will provide sufficient separation of the interior of the containment vessel from the external atmosphere, apparatus intended for use with very toxic or noxious reagents and/or to treat specimens of a toxic or otherwise dangerous nature may have more elaborate means for isolation of the containment vessel from the ambient environment. Thus the cover 26 and flange 24 may have cooperating seals (e.g. flexible, labyrinth or liquid seals) and/or means may be provided continually to withdraw atmosphere from within the containment vessel, so that all leakages are inwards to the containment vessel.

Loss of reagent by vaporization is in any event minimised as a consequence of condensation of vapour on the relatively cold surfaces of the transfer enclosure. However, this condensation may be enhanced by the provision of cooling fins on the enclosure and/or by the provision of chilled surfaces in or on the transfer enclosure, it being understood that reagent vaporization mainly takes place when the specimen basket 118 has just been raised into the enclosure and reagent is draining from the basket and specimen(s) therein. Provision may be made for collecting the condensate and for ducting it to the subjacent chamber 22.

The number of chambers may be varied to suit particular treatment procedures, and the chambers may be arranged for heating and/or cooling to maintain reagents therein at required, different, temperatures.

While in the illustrated embodiment the motor 18 is an electric motor, and solenoids and electrical position sensors are utilised to accomplish and monitor various functions, some or all of these electrically powered devices could be substituted by pneumatic or hydraulically powered devices, and electrical heaters could be substituted by hot-fluid heat-exchangers, to avoid the need for electric power to be supplied to the engine unit and into proximity to the atmosphere within the containment vessel, should this be desirable, for safety reasons, for certain uses of the apparatus.

The apparatus may be used for processing bulk tissue specimens for sectioning, or for treating slide-mounted specimen sections, e.g. in preparation for staining and coverslipping.

We claim:

1. Tissue specimen treatment apparatus comprising
(a) plurality of containers having open tops;
(b) means for transporting a specimen for treatment to selected said containers in a prescribed sequence:
(c) a containment vessel disposed about at least the open tops of said containers;
(d) cover means movable with said transporting means and enclosing the interior of said vessel so as to separate the specimen from the ambient atmosphere, said cover means being positioned to be adjacent to, and to overlie open tops of said containers; and including a transfer enclosure adapted to register with the open top of only the selected container to receive a specimen during transport thereof.

2. The apparatus of claim 1, said transfer enclosure having an access hatch therein.

3. The apparatus of claim 2, including an operating head comprising said transporting means, said cover means enclosing the operating head.

4. The apparatus of claim 3, in which said containers are arranged in a circle and said containment vessel is circular in plan.

5. The apparatus of claim 4, comprising a central engine unit for driving the transporting means and for indexing the cover means relatively to the containers.

6. The apparatus of claim 5, including a horizontal deck for supporting the containers and constituting the lower wall of said containment vessel, a peripheral flange on said deck constituting the peripheral wall of the containment vessel, said engine unit supporting said deck.

7. The apparatus of claim 6, said transporting means comprising a specimen basket, and a specimen basket manipulating mechanism, said engine unit comprising a motor and a means driven thereby and actuating said manipulating mechanism to raise and lower the specimen basket within the container vessel.

8. The apparatus of claim 7, comprising a lift cam coupled to said motor, a head carrier assembly supporting said specimen manipulating mechanism, said lift cam being rotatable relatively to the head carrier assembly to actuate said manipulating mechanism.

9. The apparatus of claim 8, comprising a one-way drive connecting said head carrier assembly to said motor whereby rotation of the motor in one direction rotates the lift cam relatively to the head carrier assembly while rotation of the motor in the opposite direction rotates the lift cam and head carrier assembly in unison.

10. The apparatus of claim 9, wherein rotation of the head carrier assembly is effective to transport said specimen basket laterally relatively to the said container with indexing of said cover means.

11. The apparatus of claim 10, including latching means for securing said head carrier assembly in a preselected indexed position relatively to said engine unit.

12. The apparatus of claim 1, including means for sealing a chamber, with a specimen therein, within the containment vessel.

13. The apparatus of claim 1, including means sealing said cover means to said containment vessel and effective to isolate the interior of the latter from the ambient temperature.

* * * * *